US009271497B2

(12) United States Patent
Lorsbach et al.

(10) Patent No.: US 9,271,497 B2
(45) Date of Patent: Mar. 1, 2016

(54) 1-(SUBSTITUTED-BENZOYL)-5-FLUORO-4-IMINO-3-METHYL-3,4-DIHYDRO-PYRIMIDIN-2(1H)-ONE DERIVATIVES

(71) Applicant: DOW AGROSCIENCES LLC, Indianapolis, IN (US)

(72) Inventors: Beth Lorsbach, Indianapolis, IN (US); W. John Owen, Carmel, IN (US); Lindsay Stelzer, Indianapolis, IN (US); Chenglin Yao, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/655,568

(22) PCT Filed: Dec. 23, 2013

(86) PCT No.: PCT/US2013/077478
§ 371 (c)(1),
(2) Date: Jun. 25, 2015

(87) PCT Pub. No.: WO2014/105821
PCT Pub. Date: Jul. 3, 2014

(65) Prior Publication Data
US 2015/0342188 A1    Dec. 3, 2015

Related U.S. Application Data

(60) Provisional application No. 61/747,128, filed on Dec. 28, 2012.

(51) Int. Cl.
A01N 43/54 (2006.01)
C07D 239/47 (2006.01)

(52) U.S. Cl.
CPC .............. *A01N 43/54* (2013.01); *C07D 239/47* (2013.01)

(58) Field of Classification Search
CPC ............................ C07D 239/47; A01N 43/54
See application file for complete search history.

(56) References Cited

U.S. PATENT DOCUMENTS

| 3,309,359 A | 3/1967 | Duschinsky et al. |
| 3,368,938 A | 2/1968 | Berger et al. |
| 3,868,373 A | 2/1975 | Hoffer |
| 4,845,081 A | 7/1989 | Sloan |
| 4,996,208 A | 2/1991 | Lindner et al. |
| 5,962,489 A | 10/1999 | Mueller et al. |
| 6,066,638 A | 5/2000 | Bereznak et al. |
| 6,617,330 B2 | 9/2003 | Walter |
| 7,914,799 B2 | 3/2011 | Jira et al. |
| 8,318,758 B2 * | 11/2012 | Boebel ................ C07D 239/47 514/274 |
| 8,470,839 B2 * | 6/2013 | Boebel ................ A01N 43/54 514/274 |
| 9,000,002 B2 * | 4/2015 | Boebel ................ A01N 47/38 514/274 |
| 9,096,627 B2 * | 8/2015 | Chen .................. C07D 235/16 |
| 2003/0039667 A1 | 2/2003 | Jira et al. |
| 2008/0004253 A1 | 1/2008 | Branstetter et al. |
| 2008/0269238 A1 | 10/2008 | Sugihara et al. |
| 2008/0280917 A1 | 11/2008 | Albrecht et al. |
| 2009/0203647 A1 | 8/2009 | Benko et al. |
| 2010/0022538 A1 | 1/2010 | Boebel et al. |
| 2011/0034491 A1 | 2/2011 | Boebel et al. |
| 2011/0034493 A1 | 2/2011 | Boebel et al. |
| 2011/0263627 A1 | 10/2011 | Boebel et al. |

FOREIGN PATENT DOCUMENTS

| EP | 0102908 A1 | 3/1984 |
| EP | 0139613 A1 | 5/1985 |
| EP | 0332579 A2 | 9/1989 |
| EP | 0877022 B1 | 4/2003 |
| GB | 989455 | 4/1965 |
| GB | 1461184 A | 1/1977 |
| JP | 6001793 A | 1/1994 |
| WO | WO9733890 A1 | 9/1997 |
| WO | WO2009/094442 A2 | 7/2009 |
| WO | WO2010047866 A2 | 4/2010 |
| WO | WO2010085377 A2 | 7/2010 |
| WO | WO2012011114 A2 | 1/2012 |
| WO | 2012108873 | 8/2012 |

(Continued)

OTHER PUBLICATIONS

Duschinsky et al., Nucleosides. XXXIII. N4-Acylated 5-Fluorocytosines and a Direct Synthesis of 5-Fluoro-2'-deoxycytidine. Journal of Medicinal Chemistry, Jul. 1, 1966, vol. 9, Nr:4, pp. 566-572.

Waring, M J, Defining optimum lipophilicity and molecular weight ranges for drug candidates-Molecular weight dependent lower logD limits based on permeability. Bioorganic & Medical Chemistry Letters, May 15, 2009, vol. 19, Nr: 10, pp. 2844-2851.

Chiacchio U, et al. Enantioselective Syntheses and Cytotoxicity of N,O-Nucleosides. Journal of Medicinal Chemistry, Jan. 1, 2003, vol. 46, pp. 3696-3702.

Morris J Robins, et al. A direct synthesis of 5-fluorocytosine and its nucleosides using trifluoromethyl hypofluorite. Journal of the Chemical Society, Chemical Communications, No. 1, Jan. 1, 1972, p. 18.

(Continued)

*Primary Examiner* — Alexander R Pagano
(74) *Attorney, Agent, or Firm* — C. W. Arnett; Faegre Baker Daniels LLP

(57) ABSTRACT

This present disclosure is related to the field of 1-(substituted-benzoyl)-5-fluoro-4-imino-3-methyl-3,4-dihydropyrimidin-2(1H)-ones and their derivatives and to the use of these compounds as fungicides. Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less. The present disclosure relates to 1-(substituted-benzoyl)-5-fluoro-4-imino-3-methyl-3,4-dihydropyrimidin-2(1H)-one compounds and their use as fungicides. The compounds of the present disclosure may offer protection against fungi and fungi like organisms including ascomycetes, basidiomycetes, deuteromycetes, and oomycetes.

7 Claims, No Drawings

(56) References Cited

FOREIGN PATENT DOCUMENTS

| WO | WO 2014105841 A1 * | 7/2014 | ............. | A01N 47/38 |
| WO | WO 2014105844 A1 * | 7/2014 | ............. | A01N 47/22 |

OTHER PUBLICATIONS

Arthur F. Lewis et al. Synthesis and in vitro anti-human cytomegalovirus (hcmv) activity of certain alkenyl substituted cytosines and 5-halocytosines. Journal of Heterocyclic Chemistry, Sep. 1, 1995, vol. 32, Nr:5, pp. 1513-1515.

Kulikowski et al. Methylation and tautomerism of 5-fluorocytosine nucleosides and their analogues. Journal Nucleic Acids Research, Jan. 1, 1978, vol. 4, pp. S7-S10.

Liang et al., A facile synthesis and herbicidal activities of novel fluorine-containing thiazolo[4,5-d] pyrimidin-7(6H)-ones. Journal of Fluorine Chemistry [online], Jul. 2007, vol. 128, Iss. 7, pp. 879-884.

Zhang et al., Improved method for synthesis of 5-fluorocytosine (5-FC). CAPLUS Abstract 111:134074 (1989).

Gabriella et al. Some 5-fluorosulfanilamidopyrimidines. Gazzetta Chimica Italiana, Jan. 1, 1963, vol. 93, Nr:10, pp. 1268-1278.

Jaworski et al. Infrared spectra and tautomerism of 5-fluorocytosine, 5-bromocytosine and 5-iodocytosine. Matrix isolation and theoretical ab initio studies. Journal of Molecular Structure, Jan. 1, 1990, vol. 223, pp. 63-92.

Bera, et al., Nucelosides with Furanyl Scaffolds, Tetrahedron 58 (2002), pp. 4865-4871.

Bera, et al. CAPLUS Abstract 137:279407 (2002), 1 page.

Duschinsky, et al., CAPLUS Abstract 61:18527 (1964), 1 page.

International Preliminary Report on Patentability for PCT/US2013/077478, dated Jun. 30, 2015, 4 pages.

International Search Report for Application No. PCT/US2013/077478, dated Apr. 28, 2014, 5 pages.

International Written Opinion for Application No. PCT/US2013/077478, dated Apr. 28, 2014, 6 pages.

Redha I.H. Al-Bayati, Suad J. Jalfta, and Sahar A. Al-Rikabi, "Synthesis of New Dihydropryimidine 2-(1H)-one Compounds," Al-Mustansiriya J. Sci., vol. 20, No. 3, pp. 53-65, 2009.

\* cited by examiner

1-(SUBSTITUTED-BENZOYL)-5-FLUORO-4-IMINO-3-METHYL-3,4-DIHYDROPYRIMIDIN-2(1H)-ONE DERIVATIVES

CROSS REFERENCE TO RELATED APPLICATIONS

This application is a U.S. National Phase Patent Application based on International Application No. PCT/US2013/077478 filed Dec. 23, 2013, which claims the benefit of U.S. Provisional Patent Application No. 61/747,128, filed on Dec. 28, 2012, the entire disclosures of which are hereby expressly incorporated herein by reference.

BACKGROUND AND SUMMARY OF THE INVENTION

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to 1-(substituted-benzoyl)-5-fluoro-4-imino-3-methyl-3,4-dihydropyrimidin-2(1H)-one compounds and their use as fungicides. The compounds of the present disclosure may offer protection against fungi and fungi like organisms including ascomycetes, basidiomycetes, deuteromycetes, and oomycetes.

One embodiment of the present disclosure may include compounds of Formula I:

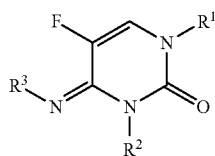

Formula I wherein $R^1$ is: —C(=O)$R^4$ or —C(=S)$R^4$;

$R^2$ is: $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_1$-$C_6$ aminoalkyl, $C_2$-$C_6$ alkylcarbonyl, arylcarbonyl, $C_2$-$C_6$ alkoxycarbonyl, $C_2$-$C_6$ alkylaminocarbonyl, —S(O)$_2R^5$, phenyl or benzyl, wherein each of the phenyl or the benzyl may be optionally substituted with 1-3 $R^5$, or a 5- or 6-membered saturated or unsaturated ring containing 1-3 heteroatoms, wherein each ring may be optionally substituted with 1-3 $R^5$;

$R^3$ is independently H, $C_1$-$C_6$ alkyl, $C_2$-$C_6$ alkenyl, $C_3$-$C_6$ alkynyl, $C_1$-$C_6$ haloalkyl, $C_1$-$C_6$ alkoxyalkyl, $C_2$-$C_6$ alkylcarbonyl, arylcarbonyl, $C_2$-$C_6$ alkoxycarbonyl, $C_2$-$C_6$ alkylaminocarbonyl, phenyl or benzyl, wherein each of the phenyl or the benzyl may be optionally substituted with 1-3 $R^5$, or a 5- or 6-membered saturated or unsaturated ring containing 1-3 heteroatoms, wherein each ring may be optionally substituted with 1-3 $R^5$;

$R^4$ is independently $C_1$-$C_6$ alkyl, $C_1$-$C_6$ haloalkyl, phenyl or benzyl, wherein each of the phenyl or the benzyl may be optionally substituted with 1-3 $R^5$, or a 5- or 6-membered saturated or unsaturated ring containing 1-3 heteroatoms, wherein each ring may be optionally substituted with 1-3 $R^5$; and $R^5$ is independently halogen, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylthio, $C_1$-$C_6$ haloalkylthio, amino, $C_1$-$C_6$ alkylamino, $C_2$-$C_6$ alkoxycarbonyl, or $C_2$-$C_6$ alkylcarbonyl, hydroxyl, cyano, or nitro.

In some embodiments, $R^4$ is phenyl optionally substituted with 1-3 $R^5$. In a more particular embodiment, $R^4$ is phenyl optionally substituted with 1-3 $C_1$ alkyl or halogen. In another more particular embodiment, $R^4$ is phenyl optionally substituted with a $C_1$ alkyl or 1-2 chloro.

In some embodiments, the compound of Formula (I) is selected from the group consisting of:

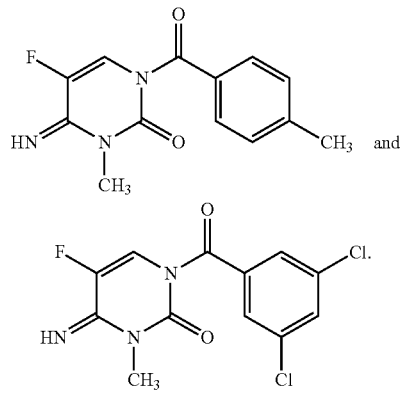

Another embodiment of the present disclosure may include a fungicidal composition for the control or prevention of fungal attack comprising the compounds described below and a phytologically acceptable carrier material.

Yet another embodiment of the present disclosure may include a method for the control or prevention of fungal attack on a plant, the method including the step of applying a fungicidally effective amount of one or more of the compounds described below to at least one of the fungus, the plant, an area adjacent to the plant, or the seed adapted to produce the plant.

Still another embodiment is A composition for the control of a fungal disease, a comprising a composition for the control of at least one fungal disease, said composition including a fungicidally effective amount of the compound of Formula I and a phytologically acceptable carrier material. In some embodiments the fungal disease is selected from the group of organisms consisting of: *Venturia inaequalis, Septoria tritici, Cercospora beticola, Cercospora arachidicola, Cercosporidium personatuml*, and *Mycosphaerella fijiensis*.

Still other embodiments include methods for the control and prevention of fungal attack on a plant, the method including the steps of: applying a fungicidally effective amount of at least one of the compounds of Formula 1 to at least one surface selected from the group of surfaces selected from the group consisting of: a portion of a plant, an area adjacent to a plant, soil in contact with a plant, soil adjacent to a plant, any surface adjacent to a plant, any surface in contact with a plant, a seed, and equipment used in agriculture. In some embodiments a fungicidally effective amount of Formula I is applied in the range of about 0.01 g/m² to about 0.45 g/m² of Formula I.

The term "alkyl" refers to a branched, unbranched, or cyclic carbon chain, including methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds, including ethenyl, propenyl, butenyl, isopropenyl, isobutenyl, cyclohexenyl, and the like.

The term "alkynyl" refers to a branched or unbranched carbon chain containing one or more triple bonds, including propynyl, butynyl and the like.

As used throughout this specification, the term 'R' refers to the group consisting of $C_{1-8}$ alkyl, $C_{3-8}$ alkenyl or $C_{3-8}$ alkynyl, unless stated otherwise.

The term "alkoxy" refers to an —OR substituent.

The term "alkoxycarbonyl" refers to a —C(O)—OR substituent.

The term "alkylcarbonyl" refers to a —C(O)—R substituent.

The term "arylcarbonyl" refers to a —C(O)—R substituent, where R is either phenyl, wherein the phenyl may be optionally substituted with 1-3 $R^5$, or a 5- or 6-membered saturated or unsaturated ring containing 1-3 heteroatoms, wherein each ring may be optionally substituted with 1-3 $R^5$.

The term "alkylsulfonyl" refers to an —$SO_2$—R substituent.

The term "alkylthio" refers to an —S—R substituent.

The term "halothio" refers to a sulfur substituted with three or five F substituents.

The term "haloalkylthio" refers to an alkylthio, which is substituted with Cl, F, I, or Br or any combination thereof The term "alkylaminocarbonyl" refers to a —C(O)—N(H)—R substituent.

The term "trialkylsilyl" refers to —$SiR_3$.

The term "cyano" refers to a —C≡N substituent.

The term "hydroxyl" refers to an —OH substituent.

The term "amino" refers to a —$NH_2$ substituent.

The term "alkylamino" refers to a —N(H)—R substituent.

The term "dialkylamino" refers to a —$NR_2$ substituent.

The term "alkoxyalkyl" refers to an alkoxy substitution on an alkyl.

The term "halogen" or "halo" refers to one or more halogen atoms, defined as F, Cl, Br, and I.

The term "nitro" refers to a —$NO_2$ substituent.

Unless specifically noted or clearly implied otherwise the term "about" refers to a range of values of plus or minus 10 percent, e.g. about 1 refers to the range 0.9 to 1.1.

Throughout the disclosure, reference to the compounds of Formula I is read as also including optical isomers and salts of Formula I, and hydrates thereof. Specifically, when Formula I contains a branched chain alkyl group, it is understood that such compounds include optical isomers and racemates thereof. Exemplary salts include: hydrochloride, hydrobromide, hydroiodide, and the like. Additionally, the compounds of Formula I may include tautomeric forms.

Certain compounds disclosed in this document can exist as one or more isomers. It will be appreciated by those skilled in the art that one isomer may be more active than the others. The structures disclosed in the present disclosure are drawn in only one geometric form for clarity, but are intended to represent all geometric and tautomeric forms of the molecule.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or seeds.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

Additional features and advantages of the present invention will become apparent to those skilled in the art upon consideration of the following detailed description of the illustrative embodiments exemplifying the best mode of carrying out the invention as presently perceived.

DETAILED DESCRIPTION OF THE DISCLOSURE

The compounds of the present disclosure may be applied by any of a variety of known techniques, either as the compounds or as formulations comprising the compounds. For example, the compounds may be applied to the roots, seeds or foliage of plants for the control of various fungi, without damaging the commercial value of the plants. The materials may be applied in the form of any of the generally used formulation types, for example, as solutions, dusts, wettable powders, flowable concentrates, suspension concentrates or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 10 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulfonic acids, oil-soluble salts or sulfated polyglycol ethers and appropriate salts of phosphated polyglycol ether.

Representative organic liquids which may be employed in preparing the emulsifiable concentrates of the compounds of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 5 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle. It is often most effective to grind and mix at the same time by preparing the aqueous mixture and homogenizing it in an implement such as a sand mill, ball mill, or piston-type homogenizer.

Aqueous emulsions comprise emulsions of one or more water-insoluble pesticidally active ingredients emulsified in an aqueous vehicle at a concentration typically in the range from about 5 to about 50 weight percent, based on the total weight of the aqueous emulsion. If the pesticidally active ingredient is a solid it must be dissolved in a suitable water-immiscible solvent prior to the preparation of the aqueous emulsion. Emulsions are prepared by emulsifying the liquid pesticidally active ingredient or water-immiscible solution thereof into an aqueous medium typically with inclusion of surfactants that aid in the formation and stabilization of the emulsion as described above. This is often accomplished with the aid of vigorous mixing provided by high shear mixers or homogenizers.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulfosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present invention in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include (RS)—N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, N-3,5-dichlorophenyl-succinimide, N-3-nitrophenylitaconimide, 2-(thiocyanatomethylthio)-benzothiazole, (3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, albendazole, aldimorph, allicin, allyl alcohol, ametoctradin, amisulbrom, amobam, Ampelomyces quisqualis, ampropylfos, anilazine, antimycin, asomate, aureofungin, azaconazole, azithiram, azoxystrobin, *Bacillus subtilis, Bacillus subtilis* strain QST713, barium polysulfide, Bayer 32394, benalaxyl, benalaxyl-M, benquinox, benodanil, benomyl, bentaluron, benthiavalicarb, benthiavalicarb-isopropyl, benthiazole, benzamacril, benzamacril-isobutyl, benzamorf, benzohydroxamic acid, benzovindiflupyr, benzylaminobenzene-sulfonate (BABS) salt, berberine, berberine chloride, bethoxazin, bicarbonates, bifujunzhi, binapacryl, biphenyl, bismerthiazol, bis(methylmercury) sulfate, bis(tributyltin) oxide, bitertanol, bithionol, bixafen, blasticidin-S, borax, Bordeaux mixture, boscalid, bromothalonil, bromuconazole, bupirimate, Burgundy mixture, buthiobate, butylamine, cadmium calcium copper zinc chromate sulfate, calcium polysulfide, *Candida oleophila*, captafol, captan, carbamorph, carbendazim, carbendazim benzenesulfonate, carbendazim sulfite, carboxin, carpropamid, carvacrol, carvone, CECA, Cheshunt mixture, chinomethionat, chitosan, chlazafenone, chlobenthiazone, chloraniformethan, chloranil, chlorfenazole, chlorodinitronaphthalenes, chlorquinox, chloroneb, chloropicrin, chlorothalonil, chlozolinate, climbazole, clotrimazole, *Coniothyrium minitans*, copper acetate, copper bis(3-phenylsalicylate), copper carbonate, basic, copper hydroxide, copper naphthenate, copper octanoate, copper oleate, copper oxychloride, copper silicate, copper sulfate, copper sulfate (tribasic), copper zinc chromate, coumoxystrobin, cresol, cufraneb, cupric hydrazinium sulfate, cuprobam, cuprous oxide, cyazofamid, cyclafuramid, cycloheximide, cyflufenamid, cymoxanil, cypendazole, cyproconazole, cyprodinil, cyprofuram, dazomet, dazomet-sodium, DBCP, debacarb, decafentin, dehydroacetic acid, diammonium ethylenebis-(dithiocarbamate), dichlofluanid, dichlone, dichloran, dichlorophen, dichlozoline, diclobutrazol, diclocymet, diclomezine, diclomezine-sodium, diethofencarb, diethyl pyrocarbonate, difenoconazole, difenzoquat ion, diflumetorim, dimetachlone, dimethirimol, dimethomorph, dimoxystrobin, dingjunezuo, diniconazole, diniconazole-M, dinobuton, dinocap, dinocap-4, dinocap-6, dinocton, dinopenton, dinosulfon, dinoterbon, diphenylamine, dipyrithione, disulfiram, ditalimfos, dithianon, dithioether, DNOC, DNOC-ammonium, DNOC-potassium, DNOC-sodium, dodemorph, dodemorph acetate, dodicin, dodicin hydrochloride, dodicin-sodium, dodine, dodine free base, drazoxolon, EBP, edifenphos, enestrobin, enestroburin, enoxastrobin, epoxiconazole, ESBP, etaconazole, etem, ethaboxam, ethirim, ethirimol, ethoxyquin, ethirimol, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenaminstrobin, fenapanil, fenarimol, fenbuconazole, fenfuram, fenhexamid, fenitropan, fenjuntong, fenoxanil, fenpiclonil, fenpropidin, fenpropimorph, fenpyrazamine, fentin, fentin acetate, fentin chloride, fentin hydroxide, ferbam, ferimzone, fluazinam, fludioxonil, flufenoxystrobin, flumetover, flumorph, fluopicolide, fluopyram, fluoroimide, fluotrimazole, fluoxastrobin, fluquinconazole, flusilazole, flusulfamide, fluthiacet-methyl, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, *Fusarium oxysporum, Gliocladium* spp., glyodine, griseofulvin, guazatine, guazatine acetates, GY-81, halacrinate, Hercules 3944, hexachlorobenzene, hexachlorobutadiene, hexachlorophene, hexaconazole, hexylthiofos, huanjunzuo, hydrargaphen, hymexazol, ICIA0858, imazalil, imazalil nitrate, imazalil sulfate, imibenconazole, iminoctadine, iminoctadine triacetate, iminoctadine tris(albesilate), inezin, iodocarb, iodomethane, ipconazole, ipfenpyrazolone, iprobenfos, iprodione, iprovalicarb, isopamphos, isoprothiolane, isopyrazam, isotianil, isovaledione, jiaxiangjunzhi, kasugamycin, kasugamycin hydrochloride hydrate, kejunlin, kresoxim-methyl, laminarin, lvdingjunzhi, mancopper, mancozeb, mandipropamid, maneb, mebenil, mecarbinzid, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl iodide, methyl isothiocyanate, methylmercury benzoate, methylmercury dicyandiamide, methylmercury pentachlorophenoxide, metiram, metominostrobin, metrafenone, metsulfovax, mildiomycin, milneb, moroxydine, moroxydine hydrochloride, mucochloric anhydride, myclobutanil, myclozolin, N-ethylmercurio-4-toluenesulfonanilide, N-(ethylmercury)-p-toluenesulphonanilide, nabam, natamycin, nickel bis(dimethyldithiocarbamate), nitrostyrene, nitrothal-isopropyl, nuarimol, OCH, octhilinone, ofurace, oleic acid (fatty acids), orysastrobin, osthol, oxadixyl, oxathiapiprolin, oxine-copper, oxpoconazole fumarate, oxycarboxin, parinol, pefurazoate, penconazole, pencycuron, penflufen, pentachlorophenol, pentachlorophenyl laurate, penthiopyrad, phenamacril, phenylmercuriurea, phenylmercury acetate, phenylmercury chloride, phenylmercury derivative of pyrocatechol, phenylmercury dimethyldithiocarbamate, phenylmercury nitrate, phenylmercury salicylate, *Phlebiopsis gigantea*, phosdiphen, phosphonic acid, phthalide, picoxystrobin, piperalin, polycarbamate, polyoxin B, polyoxins, polyoxorim, polyoxorim-zinc, potassium azide, potassium bicarbonate, potassium hydroxyquinoline sulfate, potassium polysulfide, potassium thiocyanate, probenazole, prochloraz, prochloraz-manganese, procymidone, propamidine, propamidine dihydrochloride, propamocarb, propamocarb hydrochloride, propiconazole, propineb, proquinazid, prothiocarb, prothiocarb hydrochloride, prothioconazole, pyracarbolid, pyraclostrobin, pyrametostrobin, pyraoxystrobin, pyrazophos, pyribencarb, pyributicarb, pyridinitril, pyrifenox, pyrimethanil, pyriofenone, pyrisoxazole, pyroquilon, pyroxychlor, pyroxyfur, quinacetol, quinacetol sulfate, quinazamid, quinoclamine, quinconazole, quinoxyfen, quintozene, rabenzazole, *Reynoutria sachalinensis* extract, saisentong, salicylanilide, santonin, sedaxane, silthiofam, simeconazole, sodium 2-phenylphenoxide, sodium azide, sodium bicarbonate, sodium orthophenylphenoxide, sodium pentachlorophenoxide, sodium polysulfide, spiroxamine, *Streptomyces griseoviridis*, streptomycin, streptomycin sesquisulfate, SSF-109, sulfur, sultropen, SYP-Z048, tar oils, tebuconazole, tebufloquin, tecloftalam, tecnazene, tecoram, tetraconazole, thiabendazole, thiadifluor, thicyofen, thifluzamide, thiochlorfenphim, thiodiazole-copper, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, triclopyricarb, *Trichoderma* spp., tricyclazole, tridemorph, trifloxystrobin, triflumizole, triforine, triticonazole, uniconazole, uniconazole-P, urbacid, validamycin, valifenalate, valiphenal, vangard, vinclozolin, xiwojunan, zarilamid, zineb, zinc naphthenate, zinc thiazole, ziram, and zoxamide, and any combinations thereof Additionally, the compounds of the present invention may be combined with other pesticides, including insecticides, nematocides, miticides, arthropodicides, bactericides or combinations thereof that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide, flucofuron, flucycloxuron, flucythrinate, flufenerim, flufenoxuron, flufenprox, flufiprole, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof Additionally, the compounds of the present invention may be combined with herbicides that are compatible with the compounds of the present invention in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank mixed with the herbicide(s) or applied sequentially with the herbicide(s). Typical herbicides include, but are not limited to: 4-CPA; 4-CPB; 4-CPP; 2,4-D; 2,4-D choline salt, 2,4-D esters and amines; 2,4-DB; 3,4-DA; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron-methyl, bensulide, benthiocarb, bentazon-sodium, benzadox, benzfendizone, benzipram, benzobicyclon, benzofenap, benzofluor, benzoylprop, benzthiazuron, bicyclopyrone, bifenox, bilanafos, bispyribac-sodium, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlprocarb, carfentrazone-ethyl, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop-propargyl, clofop, clomazone, clomeprop, cloprop, cloproxydim, clopyralid, cloransulam-methyl, CMA, copper sulfate, CPMF, CPPC, credazine, cresol, cumyluron, cyanatryn, cyanazine, cycloate, cyclosulfamuron, cycloxydim, cycluron, cyhalofop-butyl, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethbenzamide, ethametsulfuron, ethidimuron, ethiolate, ethobenzamid, etobenzamid, ethofumesate, ethoxyfen, ethoxysulfuron, etinofen, etnipromid, etobenzanid, EXD, fenasulam, fenoprop, fenoxaprop, fenoxaprop-P-ethyl, fenoxaprop-P-ethyl+isoxadifen-ethyl, fenoxasulfone, fenteracol, fenthiaprop, fentrazamide, fenuron, ferrous sulfate, flamprop, flamprop-M, flazasulfuron, florasulam, fluazifop, fluazifop-P-butyl, fluazolate, flucarbazone, flucetosulfuron, fluchloralin, flufenacet, flufenican, flufenpyr-ethyl, flumetsulam, flumezin, flumiclorac-pentyl, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, flurochloridone, fluroxypyr, flurtamone, fluthiacet, fomesafen, foramsulfuron, fosamine, furyloxyfen, glufosinate, glufosinate-ammonium, glyphosate, halauxifen, halosafen, halosulfuron-methyl, haloxydine, haloxyfop-methyl, haloxyfop-P-methyl, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, iofensulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, esters and amines, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, paraflufen-ethyl, parafluron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron-methyl, procyazine, prodiamine, profluazol, profluralin, profoxydim, proglinazine, prohexadione-calcium, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazogyl, pyrazolynate, pyrazosulfuron-ethyl, pyrazoxyfen, pyribenzoxim, pyributicarb, pyriclor, pyridafol, pyridate, pyriftalid, pyriminobac, pyrimisulfan, pyrithiobac-methyl, pyroxasulfone, pyroxsulam, quinclorac, quinmerac, quinoclamine, quinonamid, quizalofop, quizalofop-P-ethyl, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosate, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluron, thenylchlor, thiazafluron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr esters and amines, tridiphane, trietazine, trifloxysulfuron, trifluralin, triflusulfuron, trifop, trifopsime, trihydroxytriazine, trimeturon, tripropindan, tritac, tritosulfuron, vernolate and xylachlor.

Another embodiment of the present disclosure is a method for the control or prevention of fungal attack. This method comprises applying to the soil, plant, roots, foliage, seed or locus of the fungus, or to a locus in which the infestation is to be prevented (for example applying to cereal plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants. Additional benefits may include, but are not limited to, improving the health of a plant; improving the yield of a plant (e.g. increased biomass and/or increased content of valuable ingredients); improving the vigor of a plant (e.g. improved plant growth and/or greener leaves); improving the quality of a plant (e.g. improved content or composition of certain ingredients); and improving the tolerance to abiotic and/or biotic stress of the plant.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, wheat leaf blotch (*Mycosphaerella graminicola*; anamorph: *Septoria tritici*), apple scab (*Venturia inaequalis*), *Cercospora* leaf spots of sugar beets (*Cercospora beticola*), leaf spots of peanut (*Cercospora arachidicola* and *Cercosporidium personatum*), and black sigatoka of bananas (*Mycosphaerella fijiensis*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact amount of a compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$). Fungicidally effective amount of the compounds include amounts sufficient to kill or control true fungi, pseudo-fungi, and related organisms including water moulds.

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

The following examples are presented to illustrate the various aspects of the compounds of the present disclosure and should not be construed as limitations to the claims.

Example 1

Preparation of 5-fluoro-4-imino-3-methyl-3,4-dihydropyrimidin-2(1H)-one

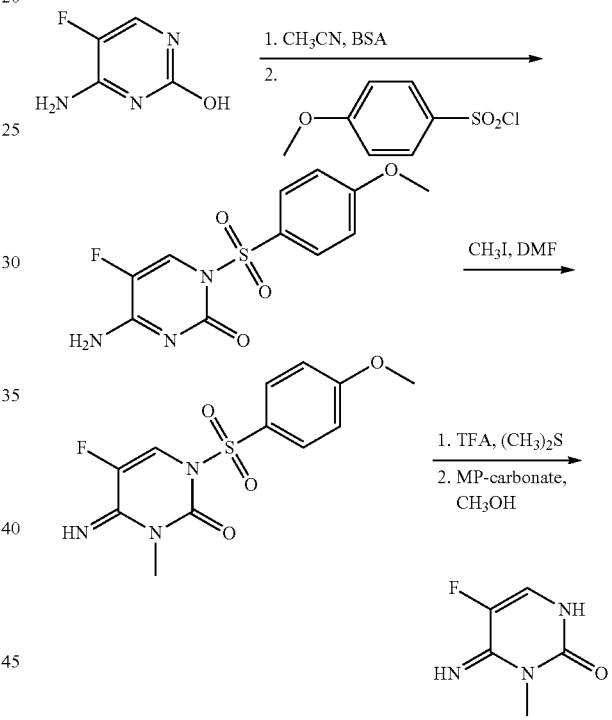

Step 1: Preparation of 4-Amino-5-fluoro-1-(4-methoxyphenylsulfonyl)pyrimidin-2(1H)-one (I-1)

To commercially available 4-amino-5-fluoro-pyrimidin-2-ol (1.0 grams (g), 7.75 millimoles (mmol)) in acetonitrile ($CH_3CN$; 50 milliliters (mL)) was added bis-N,O-trimethylsilylacetamide (BSA; 5.7 mL, 23.3 mmol) and the mixture was heated at 70° C. for 1 hour (h), resulting in a clear solution. After cooling to room temperature, 4-methoxybenzene-1-sulfonyl chloride (1.8 g, 8.5 mmol) was added, and the mixture was stirred for 24 h. The solvent was evaporated and the residue was partitioned between ethyl acetate (EtOAc) and brine. The organic phase was dried over magnesium sulfate ($MgSO_4$), filtered, and evaporated to yield the product as a pale yellow solid (1.48 g, 64%): mp 182-185° C.; $^1$H NMR (300 MHz, $CDCl_3$) δ 8.40 (br s, 1H), 8.11 (d, J=5.9 Hz, 1H), 8.04-7.98 (m, 2H), 7.02-6.96 (m, 2H), 5.77 (br s, 1H), 3.88 (s, 3H); ESIMS m/z 300 ([M+H]$^+$).

Step 2: Preparation of 5-Fluoro-4-imino-1-(4-methoxyphenylsulfonyl)-3-methyl-3,4-dihydropyrimidin-2(1H)-one (I-2)

To an 8-mL screw capped vial were added 4-amino-5-fluoro-1-(4-methoxyphenylsulfonyl)pyrimidin-2(1H)-one (0.293 g, 0.979 mmol), anhydrous potassium carbonate ($K_2CO_3$; 0.271 g, 1.96 mmol), and N,N-dimethylformamide (DMF; 4 mL), followed by iodomethane ($CH_3I$; 0.208 g, 1.47 mmol). The reaction vessel was sealed, and the reaction mixture was warmed to 60° C. and stirred for 4 h. The reaction mixture was cooled to room temperature, diluted with EtOAc (20 mL), and washed with water ($H_2O$; 3×10 mL). The organic phase was dried over $MgSO_4$, filtered, and the solvent was evaporated under reduced pressure. Purification by flash chromatography (silica gel ($SiO_2$), EtOAc/Hexanes gradient) afforded the title compound as a pale yellow solid (36 milligrams (mg), 12%): mp 158-162° C.; $^1H$ NMR (400 MHz, DMSO-$d_6$) δ 8.01 (d, J=9.22 Hz, 2H), 7.74 (d, J=5.27 Hz, 1H), 7.04 (d, J=9.23 Hz, 2H), 3.90 (s, 3H), 3.31 (s, 3H); ESIMS m/z 314 ([M+H]$^+$).

Step 3: Preparation of 5-Fluoro-4-imino-3-methyl-3,4-dihydropyrimidin-2(1H)-one (I-3)

A 25-mL screw capped vial was charged with 5-fluoro-4-imino-1-(4-methoxyphenylsulfonyl)-3-methyl-3,4-dihydropyrimidin-2(1H)-one (80.4 mg, 0.257 mmol), trifluoroacetic acid (TFA; 16.0 mL, 215 mmol), and dimethylsulfide (94 µL, 1.28 mmol). The resulting solution was allowed to stir at room temperature for 5.5 h and was then concentrated to dryness by rotary evaporation at 30° C. The crude material was then dissolved in a minimal amount of methanol ($CH_3OH$; ~2 mL) and loaded onto a 5-g normal phase solid load Isco cartridge, rinsing the source vial with $CH_3OH$ (3×1 mL). The solid cartridge was then dried under vacuum at room temperature. After drying, the product was purified by chromatography (4 g $SiO_2$ column; 0 to 30% $CH_3OH$ in dichloromethane ($CH_2Cl_2$) gradient). The material thus obtained was determined to be the 4-methoxysulfonic acid salt of the desired product. The free base was obtained by dissolving the material in $CH_3OH$ (4 mL), adding MP-carbonate resin (345 mg, 3.03 mmol/g, 4.0 equiv), and allowing to stir at room temperature. After stirring for 20 h, the solid resin was filtered off and rinsed with $CH_3OH$ (3×1 mL). After concentration under high vacuum, 5-fluoro-4-imino-3-methyl-3,4-dihydropyrimidin-2(1H)-one (35.2 mg, 96%) was obtained as a 95% pure white solid: mp 181-184° C.; $^1H$ NMR (400 MHz, DMSO-$d_6$) δ 7.48 (d, J=4.1 Hz, 1H), 3.22 (s, 3H); $^{13}C$ NMR (101 MHz, DMSO-$d_6$) δ 152.19 (s), 151.86 (d, J=27.3 Hz), 136.73 (d, J=221.0 Hz), 129.45 (d, J=26.0 Hz), 28.91 (s).

Example 2

Preparation of 1-(3,5-dichlorobenzoyl)-5-fluoro-4-imino-3-methyl-3,4-dihydropyrimidin-2(1H)-one (Compound 1)

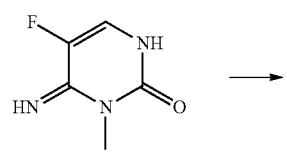

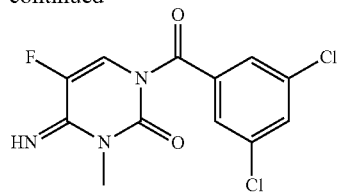

In a capped vial, (E)-trimethylsilyl-N-(trimethylsilyl)acetimidate (157 mg, 0.774) was added to 5-fluoro-4-imino-3-methyl-3,4-dihydropyrimidin-2(1H)-one (100 mg, 0.704 mmol) and acetonitrile (1.0 mL) and heated at 70° C. for 30 min. The solution was cooled to room temperature and 3,5-dichlorobenzoyl chloride (133 mg, 0.633 mmol) was added dropwise and the contents were stirred overnight at room temperature. The reaction was concentrated with a stream of nitrogen. Diethyl ether ($Et_2O$; 3 mL) was added and the vial was recapped and shaken briefly. The solids were filtered and washed with a small amount of $Et_2O$ and air dried to provide the title compound as a white solid (78 mg, 35%): mp 142-143° C.; $^1H$ NMR (400 MHz, $CDCl_3$) δ 7.65 (d, J=5.5 Hz, 1H), 7.56 (t, J=1.8 Hz, 1H), 7.49 (d, J=1.8 Hz, 2H), 3.40 (s, 3H); $^{13}C$ NMR (101 MHz, $CDCl_3$) δ 166.97, 136.71, 135.23, 135.12, 132.76, 132.37, 127.95, 126.48, 114.66, 114.27, 29.56, 29.01; ESIMS m/z 317 ([M+H]$^+$).

Example A

Evaluation of Fungicidal Activity: Leaf Blotch of Wheat (*Mycosphaerella graminicola*; Anamorph: *Septoria tritici*; Bayer Code SEPTTR)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber) to permit spores to germinate and infect the leaf. The plants were then transferred to a greenhouse for disease to develop.

The following table presents the activity of typical compounds of the present disclosure when evaluated in these experiments. The effectiveness of the test compounds in controlling disease was determined by assessing the severity of disease on treated plants, then converting the severity to percent control based on the level of disease on untreated, inoculated plants.

TABLE 1

| Compound number and structure | | | |
|---|---|---|---|
| Compound No. | Structure | Prepared as described in Example: | Precursor(s) |
| 1 | (structure shown) | 2 | As described |

TABLE 1-continued

Compound number and structure

| Compound No. | Structure | Prepared as described in Example: | Precursor(s) |
|---|---|---|---|
| 2 | 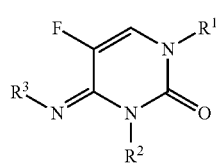 | 2 | 4-methyl-benzoyl chloride, I-3 |

TABLE 2

Compound number and analytical data

| Compound No. | Appearance | MP (° C.) | Mass | $^1$H NMR | $^{13}$C NMR |
|---|---|---|---|---|---|
| 1 | White Solid | 141.6-142.6 | ESIMS m/z 317 [M + 2H]$^+$ | $^1$H NMR (CDCl$_3$) δ 7.65 (d, J = 5.5 Hz, 1H), 7.56 (t, J = 1.8 Hz, 1H), 7.49 (d, J = 1.8 Hz, 2H), 3.40 (s, 3H) | $^{13}$C NMR (CDCl$_3$) δ 166.97, 136.71, 135.23, 135.12, 132.76, 132.37, 127.95, 126.48, 114.66, 114.27, 29.56, 29.01 |
| 2 | White Solid | 103-107 | ESIMS m/z 262 [M + H]$^+$ | $^1$H NMR (CDCl$_3$) δ 7.82 (s, 1H), 7.59 (d, J = 8.1 Hz, 2H), 7.55 (d, J = 5.5 Hz, 1H), 7.33 - 7.20 (m, 2H), 3.40 (s, 3H), 2.42 (s, 3H) | $^{13}$C NMR (CDCl$_3$) δ 169.24, 152.53, 148.45, 144.41, 138.63, 130.68, 129.15, 129.10, 115.50, 115.11, 29.49, 21.82 |

In each case of Table 3 the rating scale is as follows:

| % Disease Control | Rating |
|---|---|
| 76-100 | A |
| 51-75 | B |
| 26-50 | C |
| 0-25 | D |
| Not Tested | E |

TABLE 3

One-Day Protectant (1DP) and Three-Day Curative (3DC) Activity of Compounds vs. SEPTTR at 100 ppm

| Compound No. | SEPTTR 100 PPM 1DP | SEPTTR 100 PPM 3DC |
|---|---|---|
| 1 | A | A |
| 2 | A | A |

What is claimed is:

1. A compound of Formula I:

Formula I wherein R$^1$ is —C(═O)R$^4$ or —C(═S)R$^4$;

R$^2$ is C$_1$-C$_6$ alkyl, C$_2$-C$_6$ alkenyl, C$_3$-C$_6$ alkynyl, C$_1$-C$_6$ haloalkyl, C$_1$-C$_6$ alkoxyalkyl, C$_1$-C$_6$ aminoalkyl, C$_2$-C$_6$ alkylcarbonyl, arylcarbonyl, C$_2$-C$_6$ alkoxycarbonyl, C$_2$-C$_6$ alkylaminocarbonyl, —S(O)$_2$R$^5$, phenyl or benzyl, wherein each of the phenyl or the benzyl may be optionally substituted with 1-3 R$^5$, or a 5- or 6-membered saturated or unsaturated ring containing 1-3 heteroatoms, wherein each ring may be optionally substituted with 1-3 R$^5$;

R$^3$ is independently H, C$_1$-C$_6$ alkyl, C$_2$-C$_6$ alkenyl, C$_3$-C$_6$ alkynyl, C$_1$-C$_6$ haloalkyl, C$_1$-C$_6$ alkoxyalkyl, C$_2$-C$_6$ alkylcarbonyl, arylcarbonyl, C$_2$-C$_6$ alkoxycarbonyl, C$_2$-C$_6$ alkylaminocarbonyl, phenyl or benzyl, wherein each of the phenyl or the benzyl may be optionally substituted with 1-3 R$^5$, or a 5- or 6-membered saturated or unsaturated ring containing 1-3 heteroatoms, wherein each ring may be optionally substituted with 1-3 R$^5$;

R$^4$ is independently C$_1$-C$_6$ alkyl, C$_1$-C$_6$ haloalkyl, phenyl or benzyl, wherein each of the phenyl or the benzyl may be optionally substituted with 1-3 R$^5$, or a 5- or 6-membered saturated or unsaturated ring containing 1-3 heteroatoms, wherein each ring may be optionally substituted with 1-3 R$^5$; and R$^5$ is independently halogen, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylthio, C$_1$-C$_6$ haloalkylthio, amino, C$_1$-C$_6$ alkylamino, C$_2$-C$_6$ alkoxycarbonyl, or C$_2$-C$_6$ alkylcarbonyl, hydroxyl, cyano, or nitro.

2. The compound of Formula I, wherein the compound of Formula (I) is selected from the group consisting of:

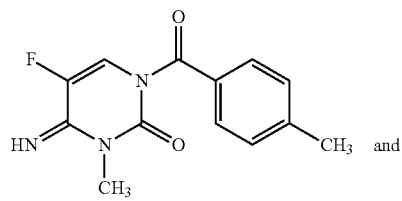 and

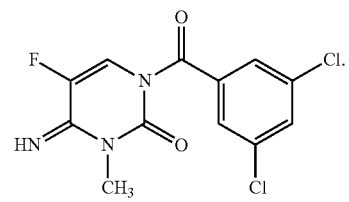

3. A composition for the control of a fungal disease, a comprising a composition for the control of at least one fungal disease, said composition including a fungicidally effective amount of the compound of Formula I and a phytologically acceptable carrier material.

4. The composition of claim 3 wherein the fungal disease is *Septoria tritici*.

5. A method for the control and prevention of fungal attack on a plant, the method including the steps of:
applying a fungicidally effective amount of at least one of the compounds of Formula (I) of claim 1 to at least one surface selected from the group of surfaces selected from the group consisting of: a portion of a plant, an area adjacent to a plant, soil in contact with a plant, soil adjacent to a plant, any surface adjacent to a plant, any surface in contact with a plant, a seed, and equipment used in agriculture.

6. The method of claim 5, wherein the fungicidally effective amount Formula I is applied to a surface in the range of about 0.01 g/m² to about 0.45 g/m² of Formula I.

7. The method of claim 5, wherein the wherein the compound of Formula (I) is selected from the group consisting of:

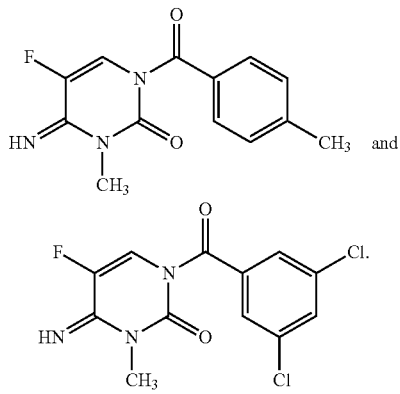

* * * * *